United States Patent
Stein et al.

(10) Patent No.: US 10,206,723 B2
(45) Date of Patent: Feb. 19, 2019

(54) ROD INSERTER AND INSERTION TUBE

(71) Applicant: Stryker European Holdings I, LLC, Kalamazoo, MI (US)

(72) Inventors: Joshua Stein, Hoboken, NJ (US); Charles L. Bush, Jr., Wayne, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 298 days.

(21) Appl. No.: 14/189,126

(22) Filed: Feb. 25, 2014

(65) Prior Publication Data

US 2014/0277205 A1 Sep. 18, 2014

Related U.S. Application Data

(60) Provisional application No. 61/781,985, filed on Mar. 14, 2013.

(51) Int. Cl.
*A61B 17/70* (2006.01)

(52) U.S. Cl.
CPC ...... *A61B 17/7086* (2013.01); *A61B 17/7083* (2013.01)

(58) Field of Classification Search
CPC ............ A61B 17/7083; A61B 17/7085; A61B 17/7086; A61B 17/7088; A61B 17/7089; A61B 17/7091; A61B 17/7077–17/708
USPC ......... 606/100, 246–279, 301, 305, 99, 104, 606/86 A; 411/393
See application file for complete search history.

(56) References Cited

U.S. PATENT DOCUMENTS

| | | | |
|---|---|---|---|
| 4,347,845 A | 9/1982 | Mayfield | |
| 4,927,425 A * | 5/1990 | Lozier | 606/99 |
| 5,020,519 A | 6/1991 | Hayes et al. | |
| 5,268,001 A | 12/1993 | Nicholson et al. | |
| 5,364,397 A | 11/1994 | Hayes et al. | |
| 5,370,646 A | 12/1994 | Reese et al. | |
| 5,707,371 A | 1/1998 | Metz-Stavenhagen | |
| 5,720,751 A | 2/1998 | Jackson | |
| 5,782,830 A | 7/1998 | Farris | |
| 5,810,878 A | 9/1998 | Burel et al. | |
| 5,910,141 A | 6/1999 | Morrison et al. | |
| 5,947,970 A | 9/1999 | Schmelzeisen et al. | |
| 6,036,692 A | 3/2000 | Burel et al. | |
| 6,123,707 A | 9/2000 | Wagner | |
| 6,139,549 A | 10/2000 | Keller | |
| 6,183,472 B1 | 2/2001 | Lutz | |
| 6,440,133 B1 | 8/2002 | Beale et al. | |
| 6,648,888 B1 | 11/2003 | Shluzas | |
| 6,660,006 B2 | 12/2003 | Markworth et al. | |
| 6,790,209 B2 | 9/2004 | Beale et al. | |
| 7,004,947 B2 | 2/2006 | Shluzas et al. | |
| 7,250,052 B2 | 7/2007 | Landry et al. | |

(Continued)

*Primary Examiner* — Ellen C Hammond
*Assistant Examiner* — Tessa Matthews
(74) *Attorney, Agent, or Firm* — Lerner, David, Littenberg, Krumholz & Mentlik, LLP

(57) ABSTRACT

A spinal rod insertion instrument includes a hollow, monolithic body having a proximal end and a distal end. The body defines a passageway that extends along a first axis between the proximal and distal ends. The distal end includes first and second arms defining a slot therebetween. The first and second arms are configured to releasably retain a spinal rod therebetween. Also provided is a method of securing a spinal rod to a coupling element attached with a pedicle screw.

17 Claims, 7 Drawing Sheets

(56) References Cited

U.S. PATENT DOCUMENTS

| | | | |
|---|---|---|---|
| 7,465,306 B2* | 12/2008 | Pond et al. | 606/86 A |
| 7,618,444 B2 | 11/2009 | Shluzas | |
| 7,776,040 B2 | 8/2010 | Markworth et al. | |
| 8,043,343 B2 | 10/2011 | Miller et al. | |
| 8,048,129 B2 | 11/2011 | Forton et al. | |
| 8,197,512 B1 | 6/2012 | Hunt et al. | |
| RE43,526 E | 7/2012 | Morrison et al. | |
| 8,439,924 B1* | 5/2013 | McBride et al. | 606/86 A |
| 9,211,149 B2* | 12/2015 | Hoefer | A61B 17/708 |
| 2005/0070901 A1* | 3/2005 | David | A61B 17/7035 606/278 |
| 2006/0111712 A1* | 5/2006 | Jackson | 606/61 |
| 2007/0078460 A1* | 4/2007 | Frigg | A61B 17/7002 606/86 A |
| 2008/0154280 A1* | 6/2008 | Schumacher | A61B 17/7083 606/104 |
| 2009/0105712 A1 | 4/2009 | Dauster et al. | |
| 2009/0157125 A1 | 6/2009 | Hoffman et al. | |
| 2010/0274252 A1* | 10/2010 | Bottomley | A61B 17/708 606/90 |
| 2011/0087298 A1* | 4/2011 | Jones | A61B 17/7086 |
| 2011/0106082 A1* | 5/2011 | Kave | A61B 17/708 606/70 |
| 2011/0166606 A1* | 7/2011 | Stihl et al. | 606/279 |
| 2011/0172714 A1* | 7/2011 | Boachie-Adjei | A61B 17/7086 606/264 |
| 2011/0276093 A1* | 11/2011 | Barrus | A61B 17/7032 606/264 |
| 2011/0319938 A1 | 12/2011 | Piza Vallespir et al. | |
| 2012/0022594 A1* | 1/2012 | Walker | A61B 17/708 606/264 |
| 2013/0046345 A1 | 2/2013 | Jones et al. | |
| 2014/0052180 A1* | 2/2014 | Justis | A61B 17/7032 606/246 |

\* cited by examiner

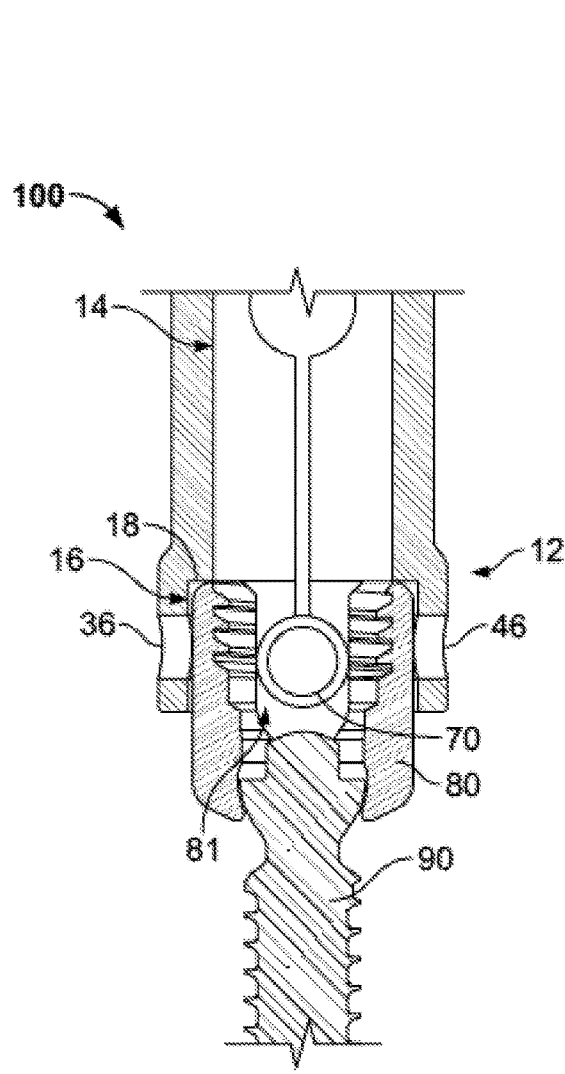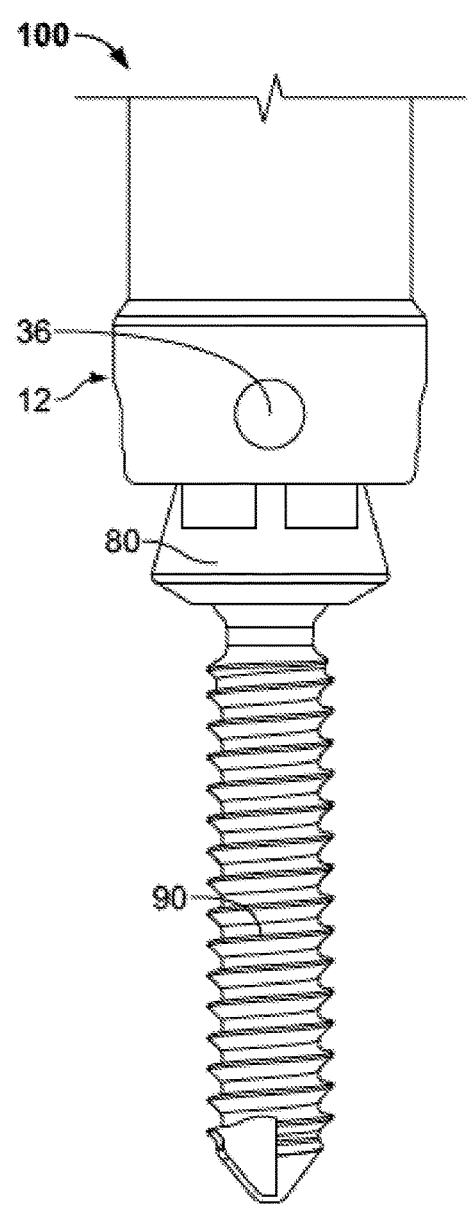
FIG. 6
FIG. 7

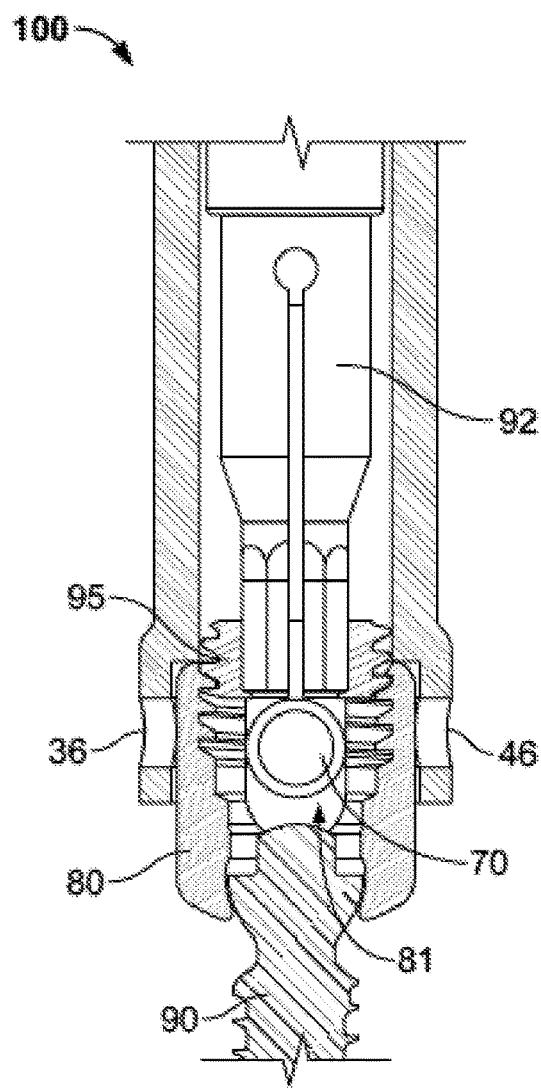
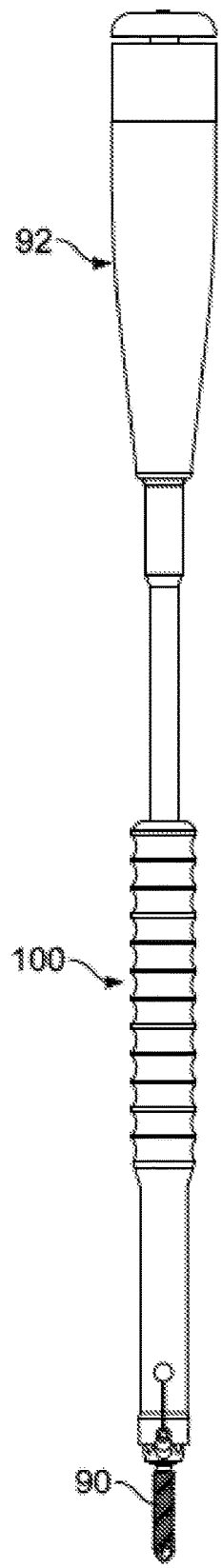
FIG. 8
FIG. 9

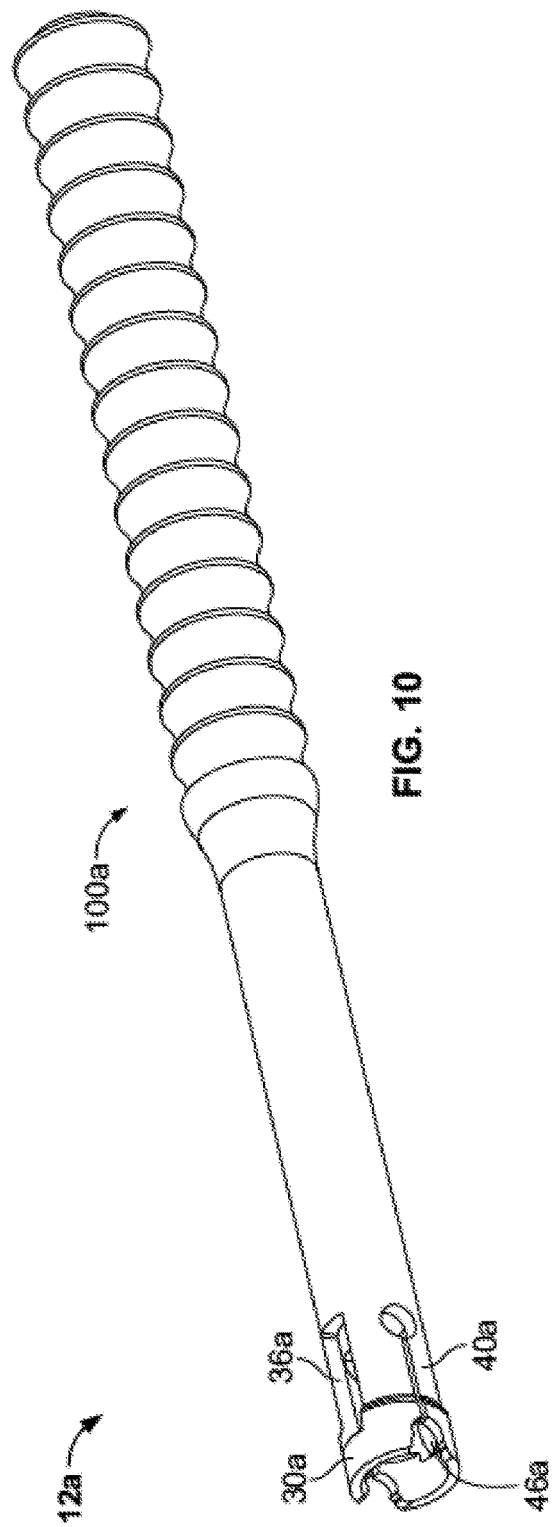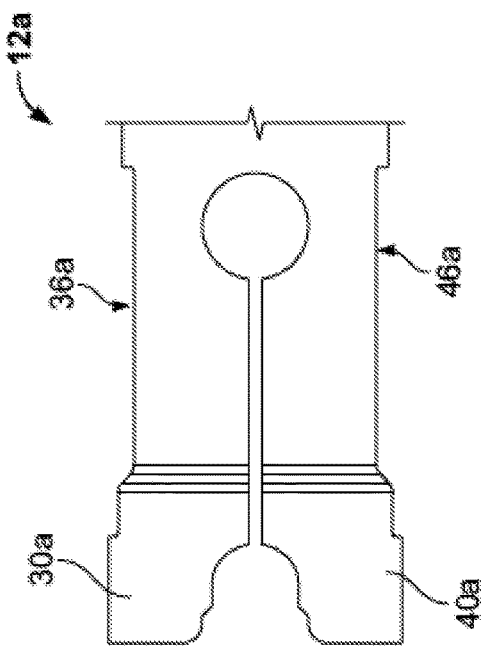

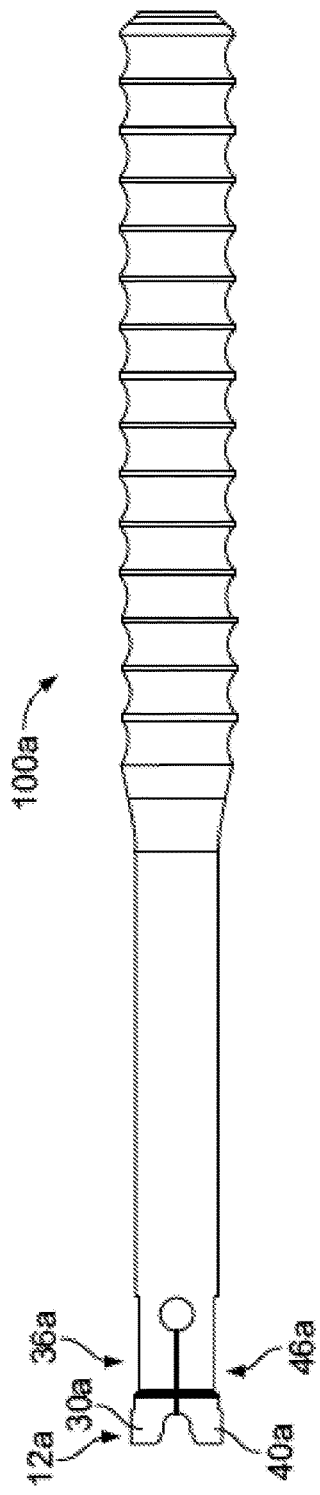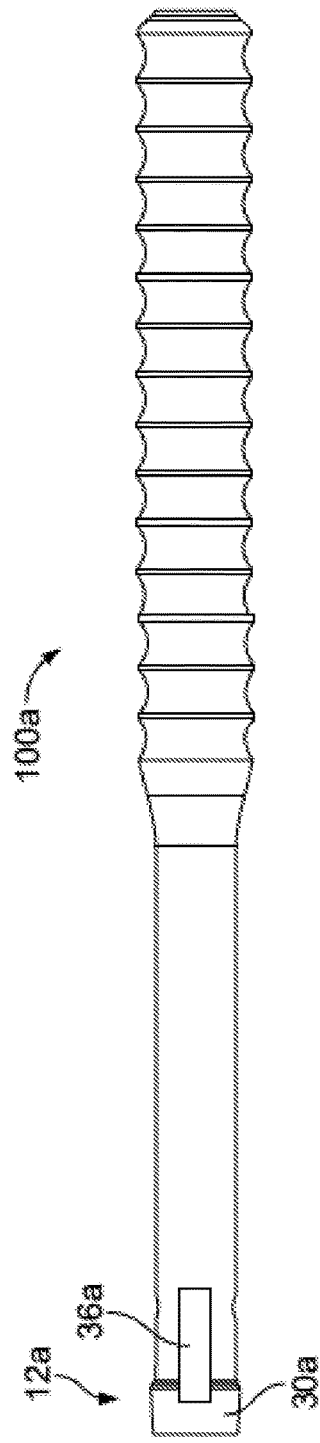

ROD INSERTER AND INSERTION TUBE

CROSS-REFERENCE TO RELATED APPLICATIONS

The present application claims the benefit of the filing date of U.S. Provisional Patent Application No. 61/781,985 filed Mar. 14, 2013, the disclosure of which is hereby incorporated herein by reference.

BACKGROUND OF THE INVENTION

The present invention relates to an instrument for urging an orthopedic rod into a recess in an orthopedic device and more particularly, to an instrument for securing a spinal rod to a coupling element.

Surgical techniques commonly referred to as spinal fixation use surgical implants and/or mechanical immobilization to fuse two or more vertebral bodies of the spinal column. Spinal fixation may also be used to alter the alignment of adjacent vertebral bodies relative to one another so as to change the overall alignment of the spinal column. Such techniques have been used effectively to treat many spinal column disorders and, in many cases, to relieve pain.

One spinal fixation technique involves immobilizing the spine using orthopedic stabilizing rods, commonly referred to as spine rods, which are positioned generally parallel to the spine. This may be accomplished by exposing the spine posteriorly and fastening bone screws to the pedicles of vertebral bodies. The pedicle screws are generally placed two per vertebra and serve as anchor points for the spine rods. Coupling elements or implants adapted for receiving a spine rod therethrough are then used to join the spine rods to the pedicle screws. A set screw or fastener then fastens the spine rod into a seat in a coupling element.

Instruments are utilized for inserting a spine rod into position within an orthopedic device such as a coupling element. Surgeons have encountered considerable difficulty when attempting to use these instruments to insert a spine rod into the seat of the coupling element and then inserting a fastener to secure the rod to the coupling element. Many of these instruments require initial insertion of the rod into the coupling element and then alignment of the instrument with the construct to ensure proper positioning of the rod. A separate instrument is typically used to insert and secure the fastener to the coupling element. Many of the current instruments are difficult to use since they require two hands, one hand to hold the instrument while it clamps the implant and one hand to operate different alignment means to properly position the rod in the implant. An entirely second instrument is often then required for inserting the fastener.

There remains a need for improved instruments for urging or persuading spinal rods into position in orthopedic devices and for securing the rods in place. Moreover, there is a need for an instrument that manipulates and positions the rod and facilitates anchoring of a subsequent fastener to hold the rod in its implanted position.

SUMMARY OF THE INVENTION

A first aspect of the present invention is a spinal rod insertion instrument including a hollow, monolithic body having a proximal end and a distal end, the body defining a passageway that extends along a first axis between the proximal and distal ends, the distal end including first and second arms defining a slot therebetween, wherein the first and second arms are configured to releasably retain a spinal rod therebetween.

In accordance with other embodiments of the first aspect, the slot may define a retaining aperture extending along a second axis perpendicular to the first axis to releasably secure the spinal rod in a fixed position with respect to the instrument. The retaining aperture may have a substantially circular cross-section in a plane perpendicular to the second axis. Each arm may include a protrusion disposed distally of the retaining aperture, and the protrusions may face each other. When the instrument is in a resting state, the retaining aperture may define a diameter and the protrusions may be separated by a first dimension perpendicular to the first axis, the diameter being larger than the first dimension. The first and second arms may include chamfered edges at a distal end of the slot, and the chamfered edges may be separated by a second dimension perpendicular to the first axis, such that when the instrument is in the resting state the second dimension is larger than the diameter.

The body may be substantially cylindrical. The passageway of the body may have a distal portion and a proximal portion, the distal portion having an inner diameter larger than an inner diameter of the proximal portion. The instrument may further include an annular shoulder disposed at a junction between the distal and proximal portions of the passageway. The arms may be moveable towards and away from each other. The body may have an outer surface that includes ribs at the proximal end. The retaining aperture may be configured to substantially match an outer contour of the spinal rod. When the instrument is in a resting state, the body may have an outer surface defining a cylindrical surface. The body may have a substantially circular cross-section in a plane perpendicular to the first axis. The first and second arms may include chamfered edges at a distal end of the slot.

A spinal rod insertion kit may include an instrument in accordance with the first aspect and a driving tool for inserting a fastener.

A spinal rod insertion kit may include a plurality of instruments in accordance with the first aspect, each having a retaining aperture of a different size.

A spinal rod insertion kit may include an instrument in accordance with the first aspect, a spinal rod, and a screw assembly including a pedicle screw, a coupling element, and a fastener. The kit may further include a driving tool for inserting the fastener.

A second aspect of the present invention is a spinal rod insertion instrument including a hollow, monolithic body having a proximal end and a distal end, the body being substantially cylindrical and defining a passageway that extends along a first axis between the proximal and distal ends, the distal end including first and second arms defining a slot therebetween, the first and second arms being configured to releasably retain a spinal rod therebetween. The slot defines a retaining aperture extending along a second axis perpendicular to the first axis to releasably secure the spinal rod in a fixed position with respect to the instrument, the retaining aperture defining a diameter when the instrument is in a resting state. Each arm includes a protrusion disposed distally of the retaining aperture, the protrusions facing each other, the protrusions being separated by a first dimension perpendicular to the first axis when the instrument is in the resting state, the diameter being larger than the first dimension. The passageway of the body has a distal portion and a proximal portion, the distal portion having an inner diameter larger than an inner diameter of the proximal portion.

In accordance with other embodiments of the second aspect, the first and second arms may include chamfered edges at a distal end of the slot, and the chamfered edges may be separated by a second dimension perpendicular to the first axis, such that when the instrument is in the resting state, the second dimension is larger than the diameter. The retaining aperture may have a substantially circular cross-section in a plane perpendicular to the second axis. The instrument may further include an annular shoulder disposed at a junction between the distal and proximal portions of the passageway. The arms may be moveable towards and away from each other.

The body may have an outer surface that includes ribs at the proximal end. The retaining aperture may be configured to substantially match an outer contour of the spinal rod. When the instrument is in a resting state, the body may have an outer surface defining a cylindrical surface. The body may have a substantially circular cross-section in a plane perpendicular to the first axis. The first and second arms may include chamfered edges at a distal end of the slot.

A spinal rod insertion kit may include an instrument in accordance with the second aspect and a driving tool for inserting a fastener.

A spinal rod insertion kit may include a plurality of instruments in accordance with the second aspect, each having a retaining aperture of a different size.

A spinal rod insertion kit may include an instrument in accordance with the second aspect, a spinal rod, and a screw assembly including a pedicle screw, a coupling element, and a fastener. The kit may further include a driving tool for inserting the fastener.

A third aspect of the present invention is a method of securing a spinal rod to a coupling element attached with a pedicle screw, the method including releasably retaining a spinal rod within a slot defined between first and second arms at a distal end of an insertion instrument, the insertion instrument including a hollow, monolithic body defining a passageway that extends along a first axis between a proximal end and the distal end, and contacting the insertion instrument with a coupling element of a screw assembly including a pedicle screw to align the spinal rod within a channel of the coupling element.

In accordance with other embodiments of the third aspect, the step of releasably retaining the spinal rod between the first and second arms may include releasably securing the spinal rod in a fixed position within a retaining aperture defined by the slot, the retaining aperture extending along a second axis perpendicular to the first axis. The method may further include engaging a fastener within the channel of the coupling element to secure the spinal rod between the coupling element and the fastener. The step of engaging the fastener within the channel of the coupling element may include inserting a driving tool through the passageway of the body. The fastener may be removably loaded onto the driver tool prior to engaging the fastener with the channel of the coupling element. The step of releasably retaining the spinal rod between the first and second arms may further include moving the spinal rod through the slot past chamfered edges at distal ends of each arm, past protrusions disposed on each arm, and into the retaining aperture. The step of releasably retaining the spinal rod between the first and second arms may include allowing the first and second arms to elastically flex away from each other. The step of releasably retaining may be carried out prior to a surgical procedure.

Other aspects of the present invention are directed to the use of a spinal rod insertion instrument according to the above aspects to secure a spinal rod to a coupling element attached with a pedicle screw.

BRIEF DESCRIPTION OF THE DRAWINGS

FIG. 6 is an enlarged front sectional view of the construct shown in FIG. 5.

FIG. 7 is an enlarged side view of the construct shown in FIG. 5.

FIG. 8 is an enlarged front sectional view of the construct shown in FIG. 5 with a fastener and a driving tool.

FIG. 9 is a front view of the construct shown in FIG. 5 with a driving tool.

FIG. 10 is a perspective view of a rod insertion instrument in accordance with another embodiment of the present invention.

FIG. 11 is an enlarged side view of the distal end of the rod insertion instrument shown in FIG. 10.

FIG. 12 is a side view of the rod insertion instrument shown in FIG. 10.

FIG. 13 is a top view of the rod insertion instrument shown in FIG. 10.

DETAILED DESCRIPTION

Figure 1:
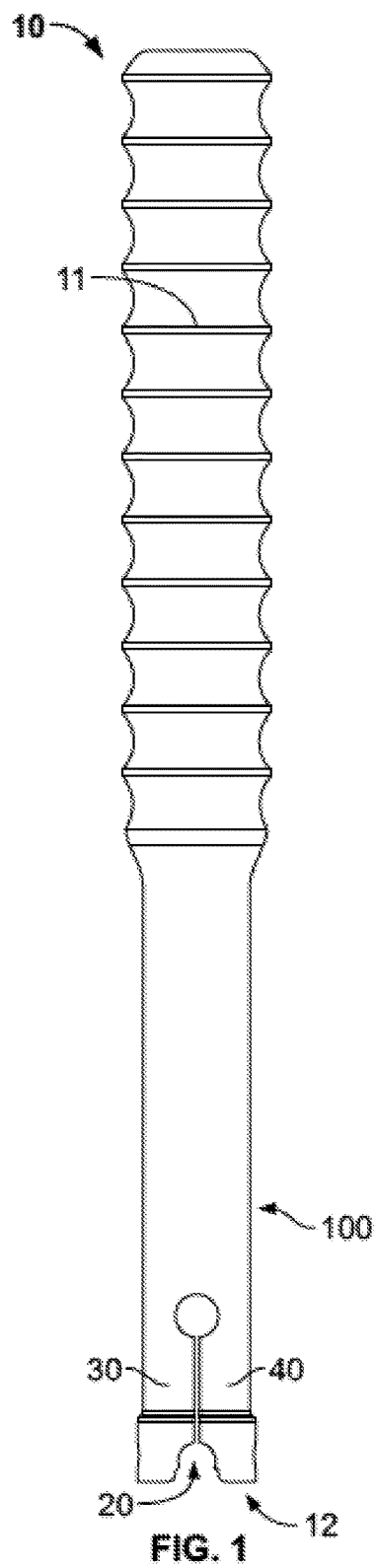
FIG. 1 is a front view of a rod insertion instrument in accordance with an embodiment of the present invention.

A rod insertion instrument 100 in accordance with an embodiment with the present invention is shown in FIGS. 1-9. Instrument 100 is configured for use in inserting a rod 70 into a coupling element 80 connected with a screw 90, shown more clearly in FIGS. 5-9. Screw 90 is typically a pedicle screw and is at least initially polyaxially connected with coupling element 80.

Instrument 100 is a generally hollow cylindrical body having a proximal end 10 and a distal end 12, which is separated by a slot 20 into a first arm 30 and a second arm 40. A distal end of slot 20 forms a rod capture mechanism 22, which is a portion of slot 20 configured to accept and temporarily retain rod 70.

Slot 20 extends axially along instrument 100 from distal end 12 toward proximal end 10. Slot 20 is open at distal end 12, thus forming arms 30 and 40 as portions of distal end 12 of instrument 100. Rod capture mechanism 22 is a contoured portion of slot 20 configured with lead-in chamfers 31, 41 on first and second arms 30, 40 that allows for easy engagement and locking with rod 70. Adjacent to chamfers 32, 42 are protrusions 34, 44 on each arm 30, 40, which open proximally into a retaining aperture 24 of slot 20. Retaining aperture 24 leads proximally into a channel 26, which leads proximally into slot end 28.

As slot 20 separates arms 30 and 40 in a hollow cylindrical body, slot 20 of course defines portions on either side of the cylindrical body. Reference to any portion of slot 20 is meant to reference both aspects thereof on either side of the cylindrical body, which aspects are preferably substantially identically dimensioned. It is contemplated that the opposing portions of the slot could be differently dimensioned to alter the movement or forces applied by the arms.

Arms 30 and 40 are moveable towards and away from each other due to the elasticity of the material of which instrument 100 is constructed and due to the configuration of slot 20. The moveable nature of arms 30 and 40 is configured in a way that allows rod 70 to be loaded into retaining aperture 24 and so that rod 70 can be releasably retained and secured within retaining aperture 24 through an interference fit in which the lateral spring forces of arms 30 and 40 with respect to the body of instrument 100 maintain a grasp on rod 70. This is enhanced by retaining aperture 24 being configured to substantially match an outer contour of rod 70.

Figure 2:
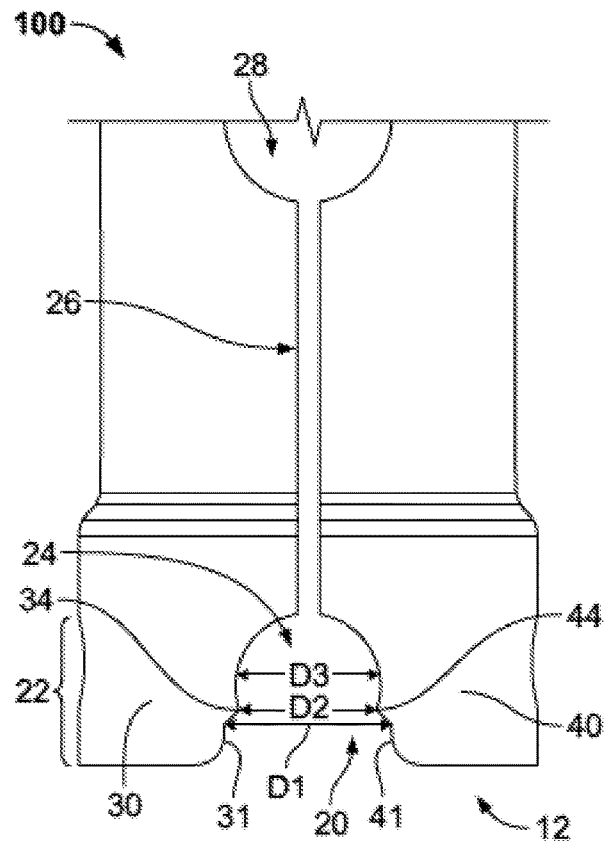
FIG. 2 is a front view of the distal end of the rod insertion instrument shown in FIG. 1.
Figure 3:
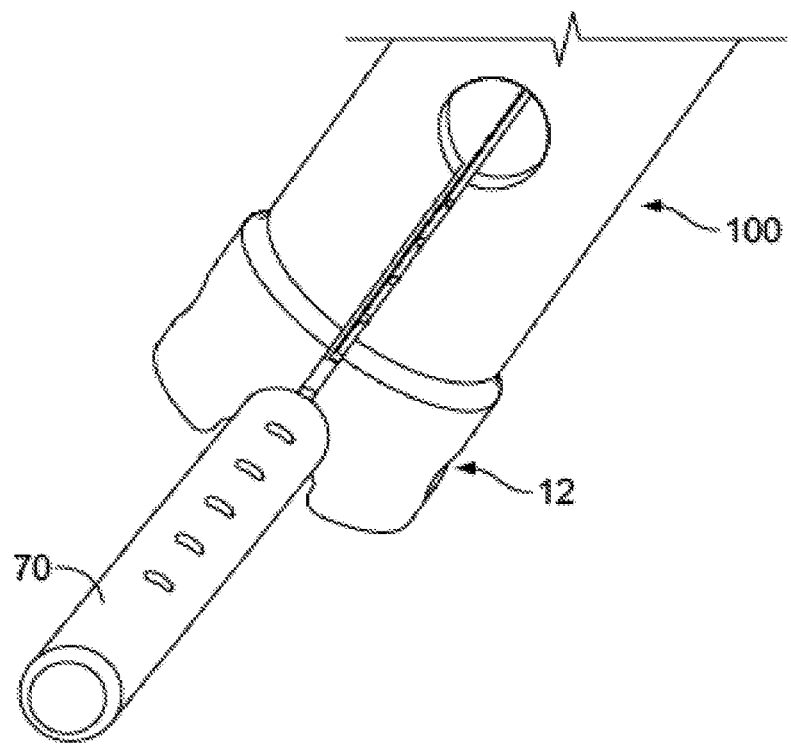
FIG. 3 is a perspective view of the distal end of the rod insertion instrument shown in FIG. 1 engaged with a rod.
Figure 4:
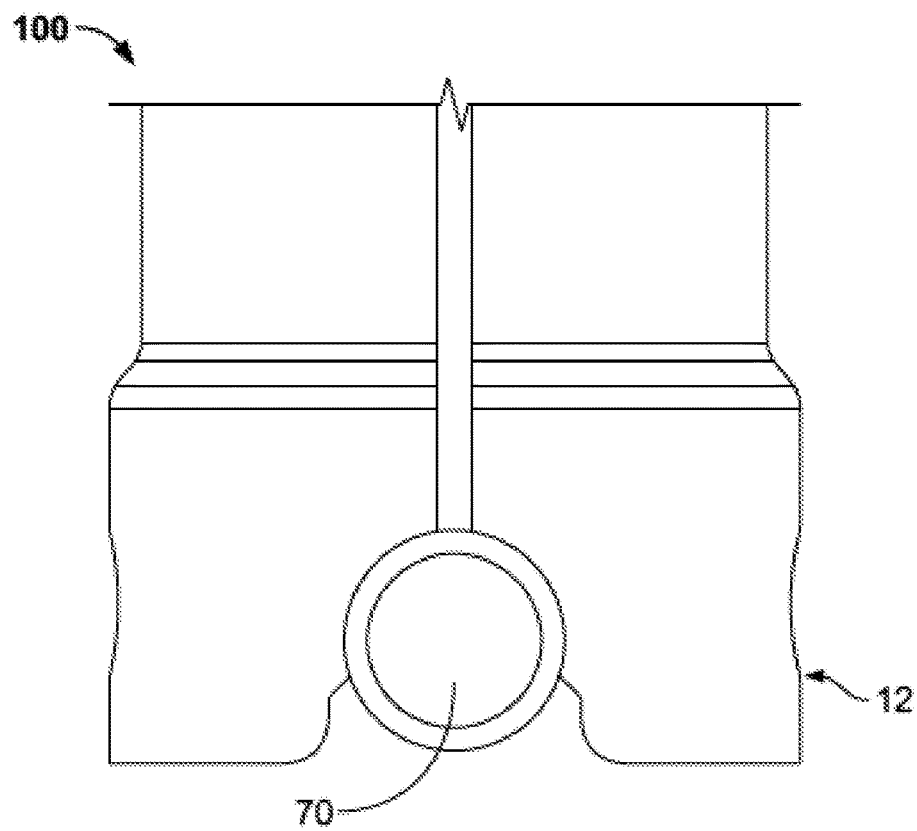
FIG. 4 is a front view of the distal end of the rod insertion instrument shown in FIG. 1 engaged with a rod.
Figure 5:
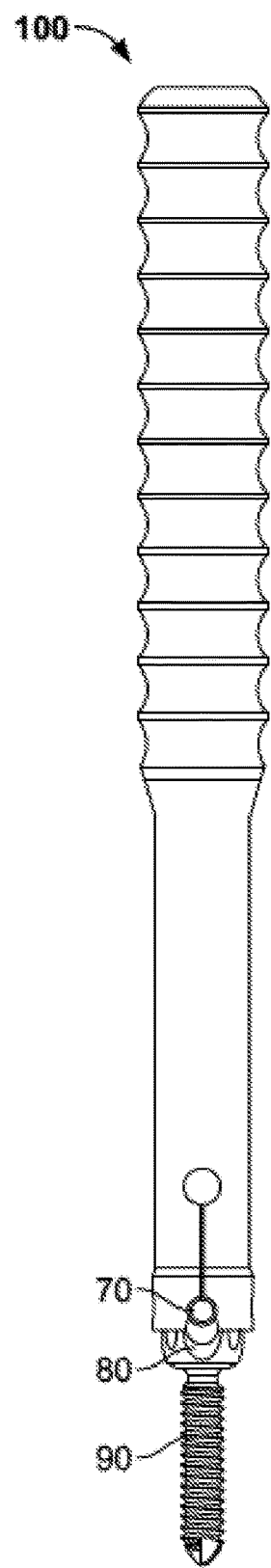
FIG. 5 is a front view of the rod insertion instrument shown in FIG. 1 engaged with a rod and a coupling element attached to a screw.

The following relative dimensions are with respect to instrument 100 in its resting state as depicted in FIGS. 1 and 2. As shown in FIG. 2, chamfers 32 and 42 are contoured to have a dimension D1 therebetween at distal end 12 that is larger than the diameter of rod 70 with which instrument 100 is configured for use, and also larger than a dimension D2 between adjacent protrusions 34, 44. This allows for rod 70 when contacting chamfers 32, 42 to be led toward retaining aperture 24. Protrusions 34 and 44 are separated by distance D2 that is smaller than the diameter of rod 70, which provides an interference or press fit once rod 70 passes protrusions 34 and 44 and is disposed within retaining aperture 24. Retaining aperture 24 has an edge that is circular and closely matches the circumference of rod 70. The diameter D3 of aperture 24 is larger than dimension D2 between protrusions 34, 44.

As shown in FIG. 6, the inner portion of distal end 12 defines a main bore 14 and a distal bore 16 of a slightly larger inner diameter than that of main bore 14. A shoulder 18 is configured as an annular seat at the junction of main bore 14 and distal bore 16. Coupling element 80 is cylindrically configured and has an outer diameter similar to or slightly less than the inner diameter of distal bore 16 and larger than the inner diameter of main bore 14. In this way, instrument 100 can be inserted over coupling element 80 up to shoulder 18, as shown in FIG. 6. Shoulder 18 will contact an upper portion of coupling element 80 to stop insertion thereof. Other features can be disposed on the inner portion of distal end 12 at distal bore 16, such as protrusions or notches, to interact with cooperating protrusions or notches on coupling element 80 to enhance the grip of instrument 100 on coupling element 80.

As shown in FIGS. 6-8, each arm 30, 40 includes a window 36, 46 that faces the other and is located at the distal end 12 of instrument. Windows 36, 46 are configured to allow a surgeon to view the components disposed within instrument 100. Particularly, visualization of proper placement of instrument 100 over coupling element 80 and of fastener 95 entering coupling element 80 is available through windows 36, 46 under fluoroscopy to determine proper placement of fastener 95. As such, the placement and configuration of windows can be widely varied and selected to facilitate this viewing purpose. In instrument 100, windows 36, 46 are circularly configured and are centrally located on each arm 30, 40. Additional windows may be provided as desired, and either or both arms may not include a window. In other embodiments, slot 20 may be configured to include a portion that acts as a window.

Proximal end 10 of instrument 100 includes ribs 11 on its external surface to provide an ergonomic, non-slip gripping surface for the surgeon. Other similar types of gripping surfaces can also or alternatively be used.

A second embodiment of a rod insertion instrument 100*a* is shown in FIGS. 10-13. Instrument 100*a* is similarly configured to instrument 100, but includes a relatively larger vertical rectangular window 36*a* in arm 30*a* at distal end 12*a*. A similarly configured window 46*a* is disposed in arm 40*a*. These windows provide a greater open area through which to view the components within instrument 100*a* through fluoroscopy during use.

In use, rod 70 can be loaded into retaining aperture 24 of instrument 100 prior to a surgical procedure. This can be done away from the patient on a preparation table, which eliminates a step that would otherwise have to be carried out during the actual surgical procedure. Rod 70 is placed into slot 20 between lead-in chamfers 32, 42 and press fit past protrusions 34, 44 into retaining aperture 24. During this step, arms 30 and 40 are allowed to elastically flex away from each other and to snap back into place once rod 70 is disposed within retaining aperture 24. This "snap" can provide a tactile and, in some cases, audible feedback to the surgeon to indicate that rod 70 is in place. Also during this step, slot end 28 is configured to permit channel 26 to widen and return to its resting state without stressing any proximal portion of instrument 100. Thus, instrument 100 can be sterilized and reused many times before needing replacement. Rod 70 can be loaded into instrument 100 either by manipulating instrument 100 against rod 70, manipulating rod 70 and placing it into a stationary instrument 100, or a combination of both.

With rod 70 disposed within retaining aperture 24 of instrument 100, instrument 100 can be located over coupling element 80, which is connected to the patient via screw 90. Distal end 12 of instrument is placed onto coupling element 80 until coupling element 80 contacts shoulder 18. As instrument 100 is located and moved into this position, captured rod 70 is automatically aligned within a U-shaped channel 81 of coupling element 80.

At this point, instrument is held in place to maintain rod 70 in this desired location while rod 70 is secured in place via a fastener 95. Insertion of fastener 95 is also facilitated by the construction of instrument 100, eliminating the need for the surgeon to switch to using an extra instrument at this point in the surgical procedure. A driving tool 92, such as a split hex-head tool, is of a dimension such that it can be inserted through instrument to gain access to coupling element 80. The inner diameter of main bore 14 of instrument is preferably at least slightly larger than the outer diameter of tool 92 and of fastener 95 to facilitate proper guidance of fastener 95 into coupling element 80 during insertion. Fastener 95 is preferably removably loaded onto the end of tool 92 and inserted through instrument 100 to a position adjacent coupling element 80. Fastener 95 is externally threaded to engage with internal threads of U-shaped channel 81 of coupling element 80. Of course, often embodiments may include an externally threaded coupling element and an internally threaded fastener.

Instrument 100 acts as a guide for at least the provisional tightening of fastener 95. As fastener 95 is threaded into coupling element 80 under the manipulation of tool 92, rod 70 is secured in place with respect to screw 90, coupling element 80, and fastener 95. During any or all of these processes for inserting rod 70 and fastener 95, visualization of proper placement of instrument 100 and the other components with respect to coupling element 80 can be gained under fluoroscopy. Windows 36, 46 may enhance the ability of the surgeon to view the components within instrument 100 during this viewing.

With fastener 95 at least provisionally secured or even fully secured, tool 92 is removed from instrument 100. It is noted that while fastener 95 is threaded into coupling element 80, the load distributed by fastener 95 to coupling element 80 during provisional tightening will cause arms 30 and 40 of instrument 100 to splay outward. This lessens or removes the forces of arms 30 and 40 on rod 70 to facilitate a release of rod 70 from the grip of instrument 100. Instrument 100 is then pulled proximally by the surgeon to remove it from coupling element 80 and rod 70. As fastener 95 is sometimes secured very tightly to the end of tool 92, removal of instrument 100 can also assist in removing tool 92 from fastener 95 as well. During removal of instrument 95, the spring forces that allow arms 30, 40 to snap over rod 70 operate similarly to allow rod 70 to slide out of retaining aperture 24 so that instrument 100 is released from the implanted construct. Instrument 100 is then removed from the surgical site.

Tool 92 can then be used to continue tightening fastener 95 with respect to coupling element 80, if desired. Instrument 100 can be located over another coupling element 80 disposed within the patient to aid in aligning rod 70 with U-shaped channel 81 of that coupling element. Nonetheless, instrument 100 offers the surgeon the ability to manipulate rod 70 into other coupling elements 80, and can facilitate insertion and at least provisional tightening of fasteners 95 at these subsequent locations. As a result, there is no need for the surgeon to switch to a separate instrument for guidance of fastener 95 into coupling element 80, either during the initial connection of rod 70 with coupling element or during subsequent couplings. Instrument 100 is therefore configured to not only capture and retain a rod in preparation for rod insertion, but can also serve as a guide for insertion of a fastener and subsequent provisional and final tightening.

While instrument 100 is configured for use with rod 70 of a particular diameter, it is contemplated that a kit of different instruments could be provided with retaining apertures 24 of relative sizes. Other dimensions of instrument 100 and slot 20 can vary accordingly to accommodate many differently sized rods. Other cross-sectional configurations of rods can also be accommodated by matching such cross-section with the configuration of retaining aperture 24. The diameters of main and distal bores 14, 16 within instrument 100 can also be varied to coordinate with different sizes of coupling elements 80. In this way, a universal kit of instruments can be provided, each configured with the novel aspects of the present invention, so that an appropriately dimensioned instrument can be selected and used by a surgeon during any one of a number of different surgical procedures. The configuration of the instruments allow for sterilization and reuse, resulting in an instrument and a kit having a long life.

One particular embodiment of instrument 100 is configured for use with a rod having a 3.5 mm diameter. With reference to FIG. 2, diameter D3 of retaining aperture 24 is also approximately 3.5 mm. Dimension D2 is approximately 3.0 mm. An outer diameter of instrument 100 at distal end 12 is approximately 11.1 mm, with other more proximal portions of the outer diameter being approximately 14.0 mm to facilitate gripping by the surgeon. This allows instrument 100 to be a low-profile construction to reduce the size and configuration of the instrument for wider applicability to surgical procedures among many patients.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A spinal rod insertion instrument comprising:
a hollow, monolithic body having a proximal end and a distal end, the body defining a passageway that extends along a first axis between the proximal and distal ends, the distal end including first and second arms defining a slot therebetween, the slot defining a retaining aperture extending along a second axis perpendicular to the first axis, the retaining aperture having a substantially circular cross-section in a plane perpendicular to the second axis, the slot further defining a channel extending proximally from the retaining aperture, the channel being configured to widen and return to a resting state;
wherein each arm includes a protrusion defined by a point on the circular cross-section, the protrusions facing each other, wherein, when the instrument is in the resting state, the retaining aperture defines an inner diameter of the circular cross-section and the protrusions are separated by a first dimension perpendicular to the first axis, the inner diameter being larger than the first dimension such that the first and second arms releasably retain a spinal rod therebetween in a fixed position along the first axis when the spinal rod is located in the retaining aperture, and
wherein a cross-section of the body in a plane perpendicular to the first axis forms a complete circle at a point along the first axis, wherein the first and second arms include chamfered edges at a distal end of the slot, the chamfered edges being separated by a second dimension perpendicular to the first axis, and wherein, when the instrument is in the resting state, the second dimension is larger than the inner diameter.

2. The instrument of claim 1, wherein the body is substantially cylindrical.

3. The instrument of claim 1, wherein the circular cross-section of the retaining aperture defines an edge that substantially matches a circumference of a spinal rod when a spinal rod is disposed therein.

4. The instrument of claim 1, wherein the passageway of the body has a distal portion and a proximal portion, the distal portion having an inner diameter larger than an inner diameter of the proximal portion.

5. The instrument of claim 4, wherein the body further includes an annular shoulder disposed at a junction between the distal and proximal portions of the passageway.

6. The instrument of claim 1, wherein a proximal end of the channel defines a circular cross-section in a plane perpendicular to the second axis, a diameter of the circular cross-section being greater than a width of the channel.

7. A spinal rod insertion kit comprising:
the instrument of claim 1, and
a driving tool for inserting a fastener.

8. A spinal rod insertion kit comprising:
a plurality of instruments as claimed in claim 1, each having a retaining aperture of a different size.

9. A spinal rod insertion kit comprising:
the instrument of claim 1,
a spinal rod, and
a screw assembly including a pedicle screw, a coupling element, and a fastener.

10. The kit of claim 9, further comprising a driving tool for inserting the fastener.

11. A spinal rod insertion kit comprising:
the instrument of claim 1, and
a spinal rod, wherein the circular cross-section of the retaining aperture defines an edge that substantially matches a circumference of the spinal rod when the spinal rod is disposed therein.

12. The spinal rod insertion kit of claim 11, wherein the spinal rod defines a rod diameter being greater than the first dimension, less than the second dimension, and substantially the same as the inner diameter of the retaining aperture.

13. A method of securing a spinal rod to a coupling element attached with a pedicle screw, the method comprising:
releasably retaining a spinal rod in a fixed position along a first axis within a slot defined between first and second arms at a distal end of a hollow, monolithic body of an insertion instrument, the body defining a passageway that extends along a first axis between a proximal end and the distal end, the retaining aperture extending along a second axis perpendicular to the first axis, the retaining aperture having a substantially circular cross-section in a plane perpendicular to the second axis, the slot further defining a channel extending proximally from the retaining aperture, the channel being configured to widen and return to a resting state; wherein each arm includes a protrusion defined by a point on the circular cross-section, the protrusions facing each other, wherein, when the instrument is in the resting state, the retaining aperture defines an inner diameter of the circular cross-section and the protrusions are separated by a first dimension perpendicular to the first axis, the inner diameter being larger than the first dimension such that the first and second arms releasably retain a spinal rod therebetween in a fixed position along the first axis when the spinal rod is located in the retaining aperture wherein a cross-section of the body in a plane perpendicular to the first axis forms a complete circle at a point along the first axis, wherein the first and second arms include chamfered edges at a distal end of the slot, the chamfered edges being separated by a second dimension perpendicular to the first axis, and wherein, when the instrument is in the resting state, the second dimension is larger than the inner diameter; and
contacting the insertion instrument with a coupling element of a screw assembly including a pedicle screw to align the spinal rod within a channel of the coupling element.

14. The method of claim 13, wherein the step of releasably retaining the spinal rod between the first and second arms includes releasably securing the spinal rod in a fixed position within a retaining aperture.

15. The method of claim 13, further comprising engaging a fastener within the channel of the coupling element to secure the spinal rod between the coupling element and the fastener.

16. The method of claim 15, wherein the step of engaging the fastener within the channel of the coupling element includes inserting a driving tool through the passageway of the body.

17. The method of claim 16, wherein the fastener is removably loaded onto the driver tool prior to engaging the fastener with the channel of the coupling element.

* * * * *